(12) United States Patent
Huang et al.

(10) Patent No.: US 11,523,208 B2
(45) Date of Patent: Dec. 6, 2022

(54) EARTIP AND A WEARABLE DEVICE INCLUDING AN EARTIP

(71) Applicant: Advanced Semiconductor Engineering, Inc., Kaohsiung (TW)

(72) Inventors: Ming-Tau Huang, Kaohsiung (TW); Yu-Jung Chang, Kaohsiung (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 0 days.

(21) Appl. No.: 16/823,074

(22) Filed: Mar. 18, 2020

(65) Prior Publication Data

US 2021/0297765 A1 Sep. 23, 2021

(51) Int. Cl.
*H04R 1/10* (2006.01)

(52) U.S. Cl.
CPC ......... *H04R 1/1041* (2013.01); *H04R 1/1016* (2013.01); *H04R 1/1058* (2013.01)

(58) Field of Classification Search
CPC .. H04R 1/1016; H04R 1/1041; H04R 1/1058; H04R 2460/11; H04R 25/652; H04R 25/02; H04R 2225/023; H04R 25/65; A61B 5/6817; A61B 5/6815
USPC ....... 381/67, 380, 312, 74, 328, 370, 56, 58; 181/135; 600/559, 301, 379
See application file for complete search history.

(56) References Cited

U.S. PATENT DOCUMENTS

| | | | |
|---|---|---|---|
| 10,835,145 B1* | 11/2020 | Prevoir | H04R 1/1016 |
| 10,860,114 B1* | 12/2020 | Oommen | G06F 3/012 |
| 2018/0235540 A1* | 8/2018 | Kirszenblat | A61B 5/14539 |
| 2019/0192077 A1* | 6/2019 | Kaiser | A61B 5/6817 |
| 2020/0107110 A1* | 4/2020 | Ji | E05F 1/1261 |
| 2021/0121116 A1 | 4/2021 | Kreuzer et al. | |

FOREIGN PATENT DOCUMENTS

| | | |
|---|---|---|
| EP | 3 415 086 A2 | 12/2018 |
| EP | 3 451 117 A1 | 3/2019 |

OTHER PUBLICATIONS

U.S. Appl. No. 17/377,168, filed Jul. 15, 2021, Lee et al.
Extended Search Report for EP Patent Application No. 21200121.8, dated Mar. 28, 2022, 7 pages.

* cited by examiner

*Primary Examiner* — Norman Yu
(74) *Attorney, Agent, or Firm* — Foley & Lardner LLP

(57) ABSTRACT

The present disclosure provides an ear tip. The ear tip includes a main body, a first conductive element at least partially embedded in the main body, a second conductive element at least partially embedded in the main body and spaced apart from the first conductive element. The main body includes a central portion having a top and a tail portion extending from the top of the central portion. The first conductive element is proximal to the top of the central portion and the second conductive element is distal from the top of the central portion. A wearable device is also disclosed.

9 Claims, 10 Drawing Sheets

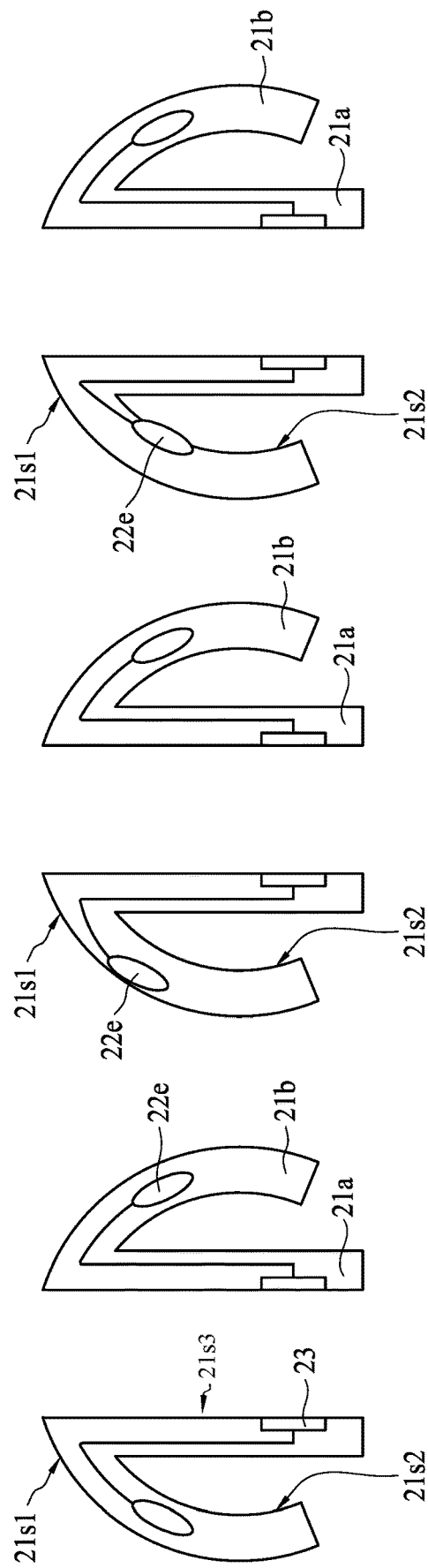

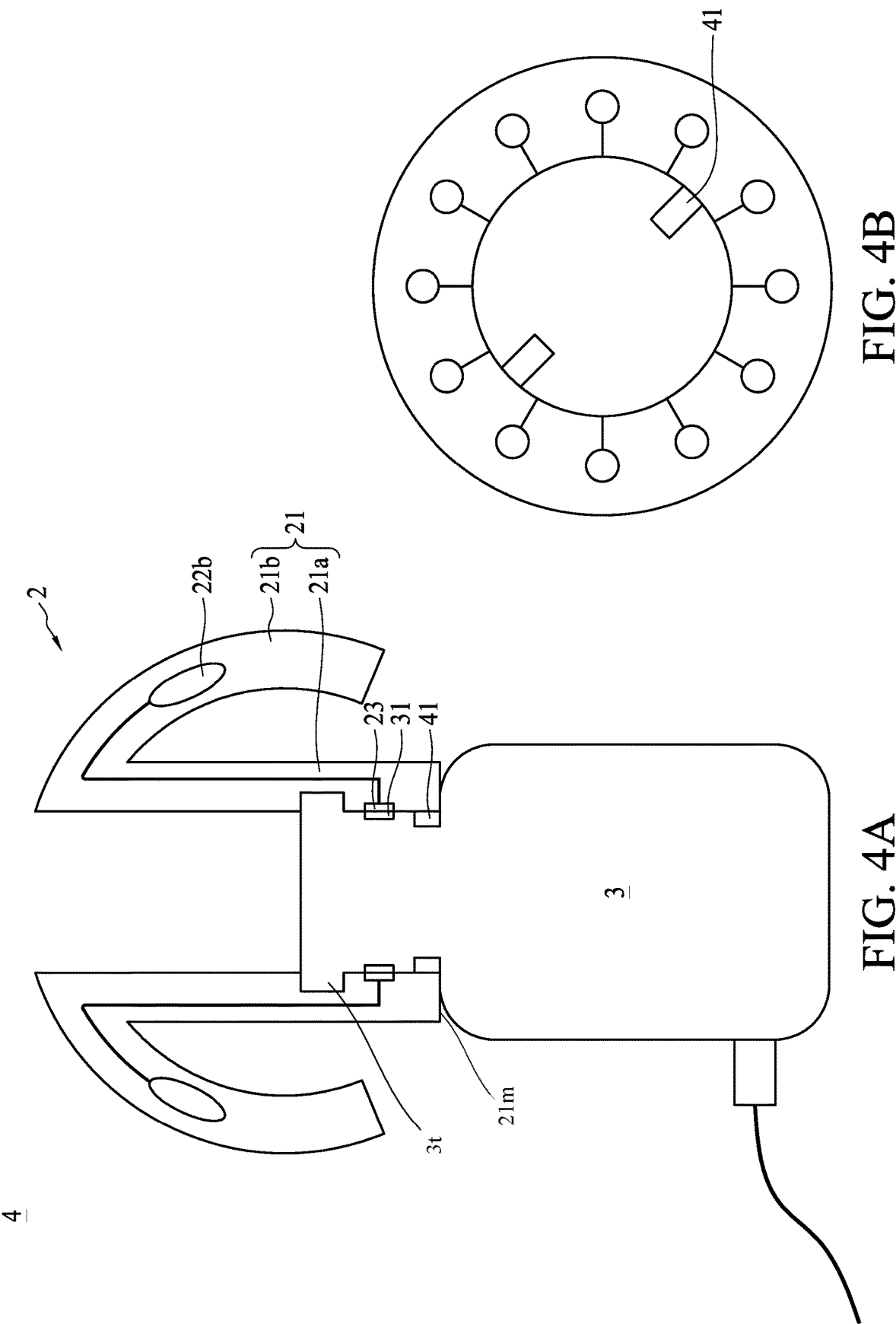

EARTIP AND A WEARABLE DEVICE INCLUDING AN EARTIP

1. TECHNICAL FIELD

The present disclosure generally relates to an ear tip and, in particular, to an ear tip with a conductive element embedded therein.

2. DESCRIPTION OF THE RELATED ART

Monitoring biologically-relevant information helps determine a wide array of an individual's physiological characteristics. Integrating a monitoring device (such as a sensor) with a wearable device (such as an earpiece) allows pertinent information to be collected in a continuous and non-intrusive manner, and thus has become increasingly popular.

SUMMARY

In one or more embodiments, the present disclosure provides an ear tip. The ear tip includes a main body, a first conductive element at least partially embedded in the main body, a second conductive element at least partially embedded in the main body and spaced apart from the first conductive element. The main body includes a central portion having a top and a tail portion extending from the top of the central portion. The first conductive element is proximal to the top of the central portion and the second conductive element is distal from the top of the central portion.

In one or more embodiments, the present disclosure provides an ear tip. The ear tip includes a main body and a proximity sensor at least partially embedded in the main body. The main body includes a central portion having a top and a tail portion extending from the top of the central portion.

In one or more embodiments, the present disclosure provides a wearable device. The wearable device includes an ear tip. The ear tip includes a main body including a central portion having a top and a bottom opposite to the top, a first conductive pad surrounded by the central portion of the main body, and a second conductive pad surrounded by the central portion of the main body and spaced apart from the first conductive pad. The wearable device includes a housing configured to be adapted in the bottom of the central portion. The housing includes a third conductive pad arranged in corresponding to the first conductive pad, and a fourth conductive pad arranged in corresponding to the second conductive pad. The first conductive pad is proximal to the bottom of the central portion and the second conductive pad is distal from the bottom of the central portion.

BRIEF DESCRIPTION OF THE DRAWINGS

Aspects of the present disclosure are readily understood from the following detailed description when read with the accompanying figures. It should be noted that various features may not be drawn to scale. The dimensions of the various features may be arbitrarily increased or reduced for clarity of discussion.

FIG. 3A illustrates a cross-sectional view of an ear tip in accordance with some embodiments of the present disclosure.

FIG. 3B illustrates a cross-sectional view of an ear tip in accordance with some embodiments of the present disclosure.

FIG. 3C illustrates a cross-sectional view of an ear tip in accordance with some embodiments of the present disclosure.

FIG. 4A illustrates a cross-sectional view of a wearable device in accordance with some embodiments of the present disclosure.

FIG. 4B illustrates a top view of an ear tip in accordance with some embodiments of the present disclosure.

Common reference numerals are used throughout the drawings and the detailed description to indicate the same or similar elements. The present disclosure will be more apparent from the following detailed description taken in conjunction with the accompanying drawings.

DETAILED DESCRIPTION

Figure 1:
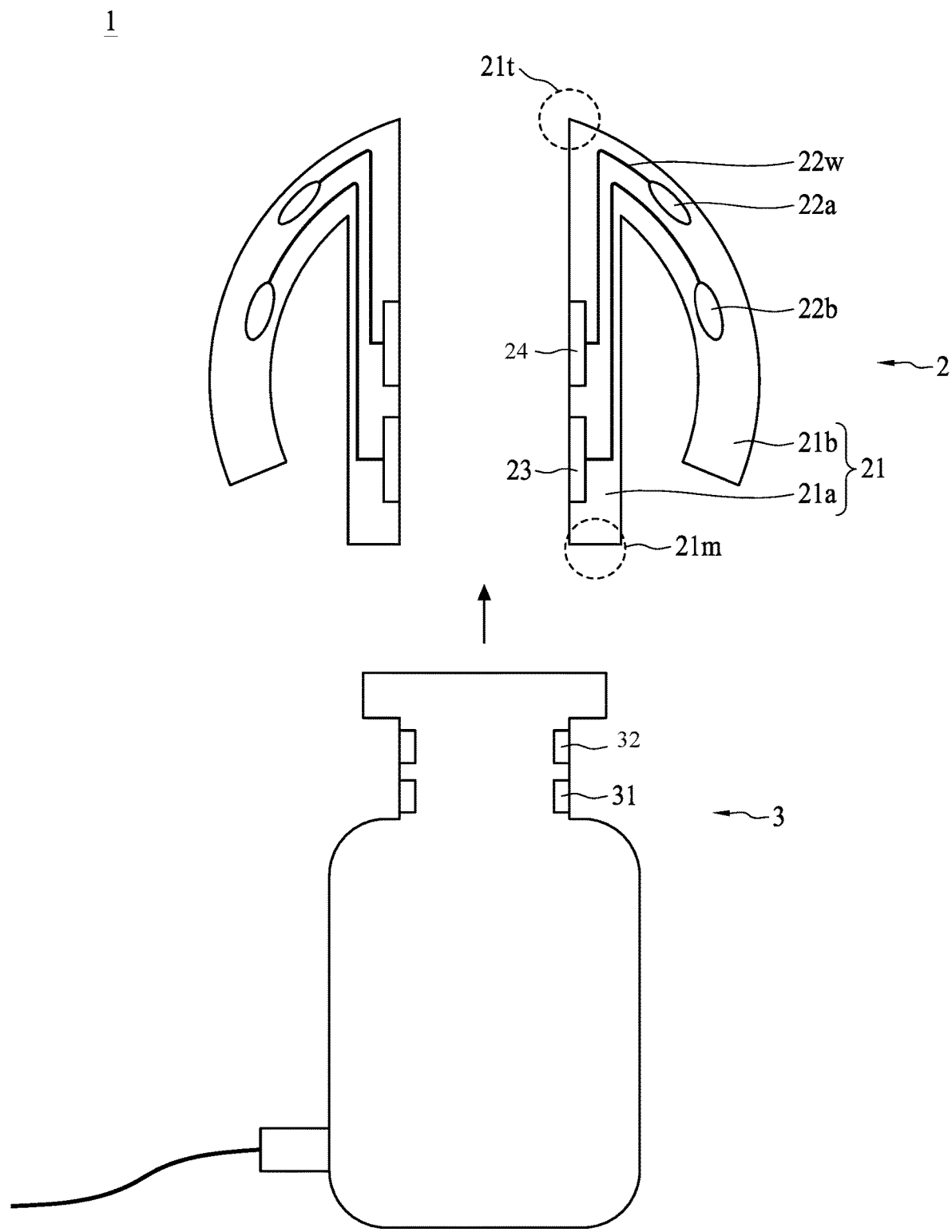
FIG. 1 illustrates a cross-sectional view of a wearable device in accordance with some embodiments of the present disclosure.

The following disclosure provides for many different embodiments, or examples, for implementing different features of the provided subject matter. Specific examples of components and arrangements are described below. These are, of course, merely examples and are not intended to be limiting. In the present disclosure, reference to the formation of a first feature over or on a second feature in the description that follows may include embodiments in which the first and second features are formed in direct contact, and may also include embodiments in which additional features may be formed between the first and second features, such that the first and second features may not be in direct contact. Besides, the present disclosure may repeat reference numerals and/or letters in the various examples. This repetition is for simplicity and clarity and does not in itself dictate a relationship between the various embodiments and/or configurations discussed.

Embodiments of the present disclosure are discussed in detail below. It should be appreciated, however, that the present disclosure provides many applicable concepts that can be embodied in a wide variety of specific contexts. The specific embodiments discussed are merely illustrative and do not limit the scope of the disclosure.

Referring to FIG. 1, FIG. 1 illustrates a cross-sectional view of a wearable device (such as an earpiece) 1 in accordance with some embodiments of the present disclosure. The wearable device 1 includes an ear tip 2 and a housing 3. The housing 3 may be fitted or received in the ear tip 2. In some embodiments, the housing 3 may be internal to the ear tip 2.

The application or usage of the ear tip 2 illustrated in the figures are for illustrative purpose only, and are not intended to limit the present disclosure. For example, the ear tip 2 of the present disclosure can be used in combination with any wearable device. For example, in some embodiments, the ear tip 2 of the present disclosure can be used in combination with a piece of equipment that transmitting audio signals. In some embodiments, the ear tip 2 of the present disclosure can be used in combination with a detecting device, an electronic device (such as a signal processing device) and/or other corresponding external device for further processing electrical signals collected through the ear tip 2. In some embodiments, the ear tip 2 of the present disclosure can be used as ear plugs, such as ear plugs for sleeping.

As shown in FIG. 1, the ear tip 2 includes a main body 21, conductive elements 22a and 22b, a conductive wire 22w, and conductive pads 23 and 24.

In some embodiments, from a side view, the main body 21 of the ear tip 2 includes a central portion 21a and a tail portion 21b (or two arms) extending from the central portion 21a. In some embodiments, from a top view (such as the top view of FIG. 2A), the main body 21 may include, for example, a basically disc-, donut-(torus-) shape and/or ellipsoid form.

The central portion 21a of the main body 21 has a top 21t and a bottom 21m opposite to the top 21t. When the wearable device 1 is worn by a user, the top 21t of the ear tip 2 sits more deeply into the ear canal than does the bottom 21m. In some embodiments, while the wearable device 1 is worn by a user, the top 21t is closer, than the bottom 21m, to a blood vessel (such as the internal carotid artery or the internal jugular vein) of the user. The bottom 21m may be adapted or shaped to receive the housing 3 of the wearable device 1.

In some embodiments, the main body 21 may include, for example, rubber, silicon, sponge, or other suitable material such as an elastic material, a soft material, or a flexible material. The main body 21 may be soft and flexible enough for the user to wear for an extended time period without feeling uncomfortable.

The conductive elements 22a and 22b are arranged in the tail portion 21b of the main body 21, while the conductive pads 23 and 24 are arranged in the central portion 21a of the main body 21. The conductive elements 22a and 22b are electrically connected to the corresponding conductive pads 23 and 24 for signal transmission.

The conductive elements 22a and 22b are disposed in a space defined by the main body 21. For example, the conductive elements 22a and 22b are surrounded, embedded, or covered by the main body 21. In some embodiments, as shown in FIG. 1, the conductive elements 22a and 22b are entirely embedded in the main body 21.

In some embodiments, the conductive elements 22a and 22b may be used to collect one or more information associated with the user of the earpiece. In some embodiments, the conductive elements 22a and 22b may be used to collect one or more of a pulse travel time (PTT), an electroencephalogram (EEG), electrocardiogram (ECG), electromyogram (EMG), electrooculogram (EOG), galvanic skin response (GSR), sweat composition, pH, or other biologically-relevant information associated with the user of the earpiece. For example, the electrical signals collected by the conductive elements 22a and 22b may be used to produce an ECG from a user.

The housing 3 may include, for example, conductive pads 31 and 32 and an electronic device (not shown in the figures). In some embodiments, the conductive pad 31 may be arranged at a location corresponding to the conductive pad 23, and the conductive pad 32 may be arranged at a location corresponding to the conductive pad 24. For example, the conductive pad 23 and the conductive pad 31 may be in contact with each other while the housing 3 is received in the ear tip 2. The electrical signals collected via the conductive elements 22a and 22b may be transmitted to the electronic device in the housing 3 through the conductive wire 22w, the conductive pads 23 and 24, and the conductive pads 31 and 32. Then, the electrical signals may be transmitted to an outer apparatus or device (such as an ECG machine) for being further processed.

As shown in FIG. 1, the distance between the top 21t and the conductive element 22a is different from the distance between the top 21t and the conductive element 22b. For example, the conductive element 22a and the conductive element 22b are arranged at different distances measured from the top 21t. For example, the conductive element 22a and the conductive element 22b are arranged at different elevations with respect to the top 21t. For example, the conductive element 22a is closer to or proximal to the top 21t in comparison with the conductive element 22b. For example, the conductive element 22b is farther or distal from the top 21t in comparison with the conductive element 22a.

Similarly, the distance between the top 21t and the conductive pad 23 is different from the distance between the top 21t and the conductive pad 24. For example, the conductive pad 24 is closer to or proximal to the top 21t (or is farther or distal from the bottom 21m) in comparison with the conductive pad 23. For example, the conductive pad 23 is farther or distal from the top 21t (or is closer to or proximal to the bottom 21m) in comparison with the conductive pad 24.

By arranging the conductive element 22a and the conductive element 22b at different distances measured from the top 21t, the conductive element 22a may be closer to a blood vessel (such as the internal carotid artery or the internal jugular vein) of the user while the wearable device 1 being worn. As a result, the electrical signals received via the conductive element 22a may be different from the electrical signals received via the conductive element 22b. The electrical signals received via the conductive element 22a and the conductive element 22b may be used as a positive potential reference and a negative potential reference, respectively, or vice versa.

The wide potential difference (or variation, gap) between the positive potential reference and the negative potential reference can help remove uncorrelated noise which may be present in the electrical signals. Therefore, since the conductive element 22a and the conductive element 22b are arranged at different distances from the top 21t according to the present disclosure, a good signal to noise ratio can be obtained, and the electrical signals collected by the conductive elements of the ear tip 2 can be enhanced.

In some existing approaches, the ear tip is coated with a continuous conductive coating, which may get damaged or become distorted by constant rubbing, possibly causing the collected electrical signals to be incorrect. In contrast, the conductive element 22a and the conductive element 22b are protected by the main body 21 according to the present disclosure; as such, the problem of the existing approaches can be solved.

Furthermore, unlike the electrical sensing methods according to the present disclosure, in some existing approaches, the biologically-relevant information may be collected through a light sensing element. However, light may be a variable which may affect the collected data and cause measurement error. For example, if insufficient light is reflected in the ear canal of a user, the collected data may be insufficient or incorrect. By collecting the data through electrical sensing methods, the problem of the existing approaches can be solved.

Figure 2A:
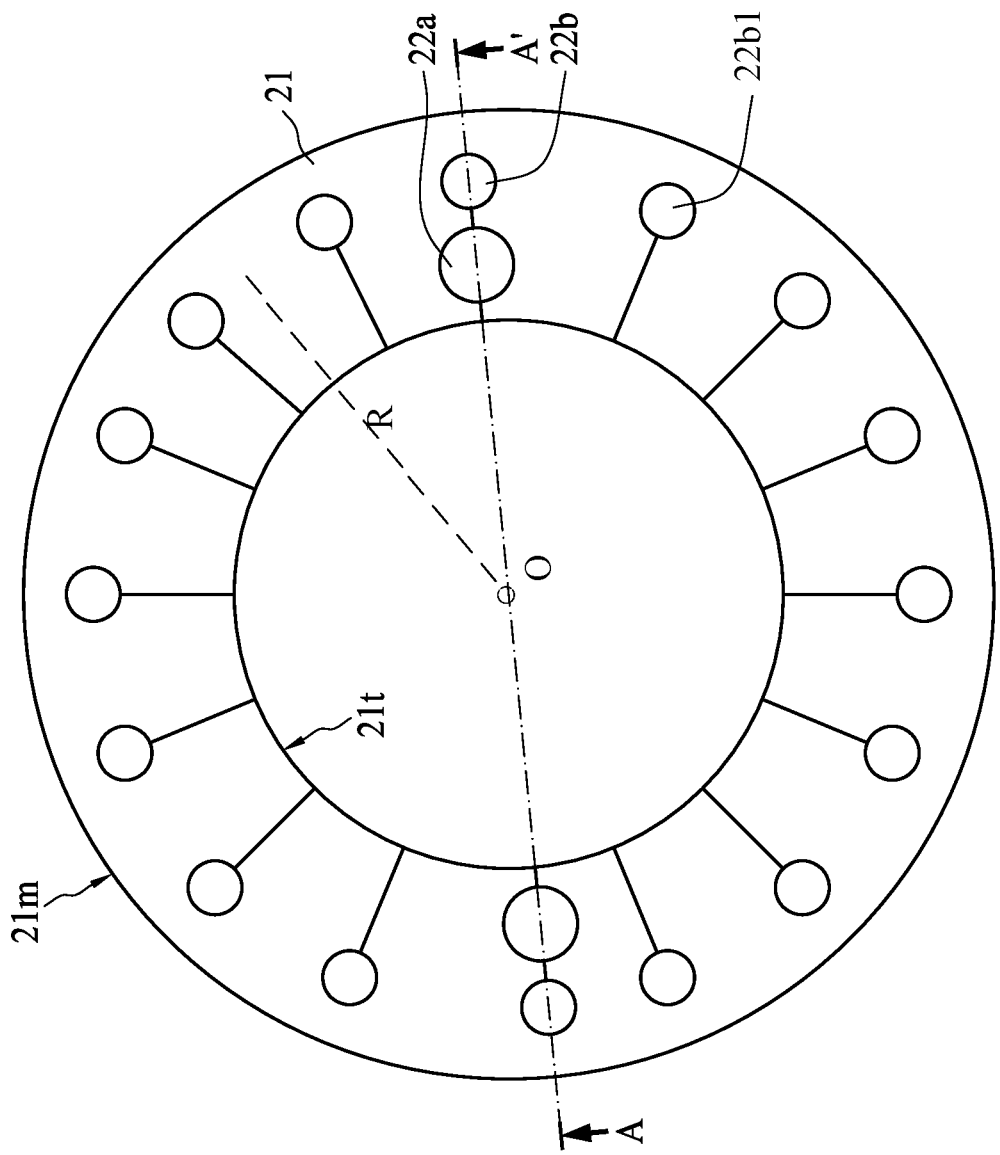
FIG. 2A illustrates a top view of an ear tip in accordance with some embodiments of the present disclosure.

Referring to FIG. 2A, FIG. 2A illustrates a top view of an ear tip in accordance with some embodiments of the present disclosure. In some embodiments, the ear tip 2 of FIG. 1 may be a cross-sectional view of the ear tip of FIG. 2A taken along line AA'.

As shown in FIG. 2A, the conductive element 22a is disposed closer to the top 21t, and the conductive element 22b is disposed closer to the bottom 21m.

In some embodiments, the conductive element 22a and the conductive element 22b are partially overlapped from the top view. For example, the conductive element 22a and the conductive element 22b are partially overlapped in a direction from the central portion 21a to the tail portion 21b. For example, the conductive element 22a and the conductive element 22b are partially overlapped in a direction from the top 21t to the bottom 21m. For example, the conductive element 22a and the conductive element 22b are partially overlapped in a radial direction of the central portion 21a.

In some embodiments, as shown in FIG. 2A, the conductive element 22b and the conductive element 22b1 are spaced apart from each other. In some embodiments, the conductive element 22b and the conductive element 22b1 are partially overlapped in a direction surrounding the central portion 21a. For example, the conductive element 22b and the conductive element 22b1 are partially overlapped in a tangent direction of the central portion 21a. For example, a circumference of an imaginary circle with center of O and radius equal to R may cross or pass through the conductive element 22b and the conductive element 22b1.

In some embodiments, a central angle defined by two of the adjacent conductive elements (such as the conductive element 22b and the conductive element 22b1) may be less than 180 degrees, less than 120 degrees, less than 90 degrees, less than 60 degrees, less than 30 degrees, or less.

In some embodiments, the conductive element 22a and the conductive element 22b may include an electrode. In some embodiments, an ECG signal may be measured based on the electronic signals received from the electrodes in the ear tip 2. The greater number of electrodes in the ear tip 2 (and therefore, the more data can be collected, processed, and calculated) may help correct the collected signals, remove noise, and improve accuracy of the produced data. For example, the potential difference among the conductive element 22a, the conductive element 22b, and the conductive element 22b1 can help remove uncorrelated noise and enhance the electrical signals collected.

The positions and the numbers of the conductive elements in the ear tip 2 illustrated in the figures are for illustrative purpose only, and are not intended to limit the present disclosure. For example, there may be any number of conductive elements in the ear tip 2 due to design requirements. For example, the conductive elements in the ear tip 2 may be arranged in any position due to design requirements.

Figure 2D:
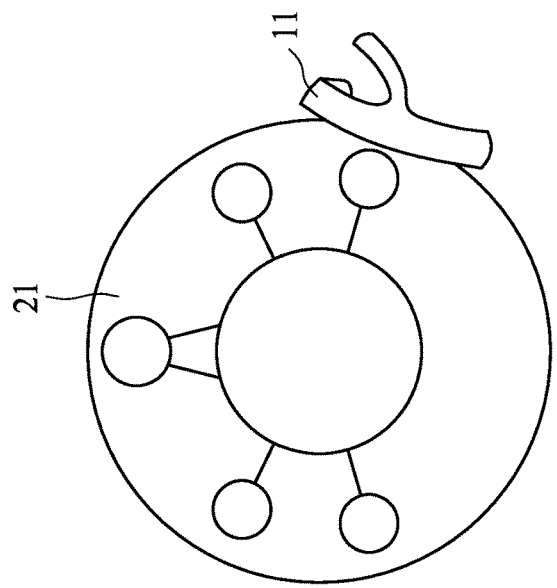
FIG. 2D illustrates a top view of an ear tip being used in accordance with some embodiments of the present disclosure.
Figure 2C:
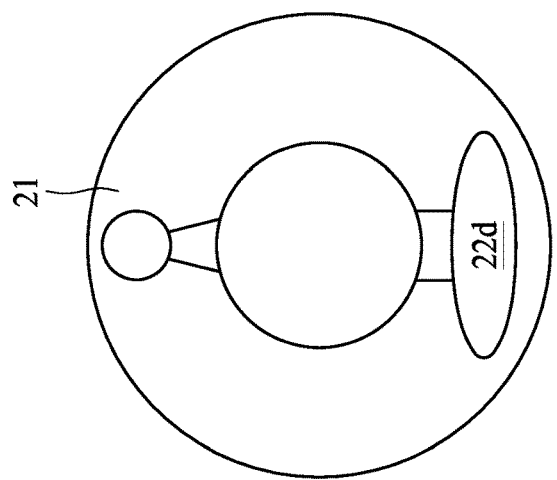
FIG. 2C illustrates a top view of an ear tip in accordance with some embodiments of the present disclosure.
Figure 2B:
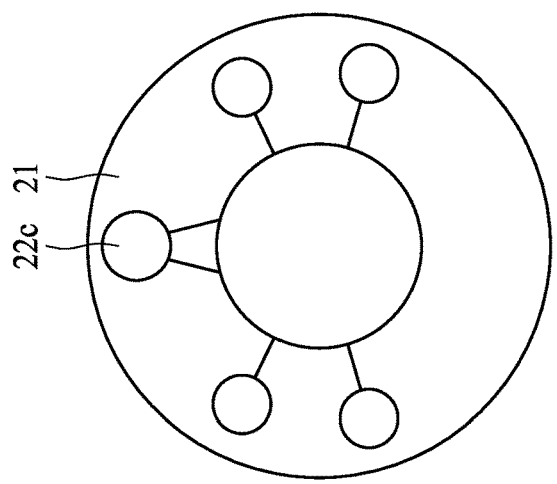
FIG. 2B illustrates a top view of an ear tip in accordance with some embodiments of the present disclosure.

Referring to FIG. 2B, FIG. 2B illustrates a top view of an ear tip in accordance with some embodiments of the present disclosure. The ear tip of FIG. 2B is similar to the ear tip 2 of FIG. 2A, and the differences therebetween are described below.

The ear tip of FIG. 2B further includes a thermistor 22c disposed in the main body 21. In some embodiments, while being worn by a user, the thermistor 22c may be in contact with the human body for a sufficient duration in which to reach thermal equilibrium, and the temperature of the user can be obtained through the voltage and/or resistance measurement using the thermistor 22c. As mentioned, since the temperature of the user is obtained through an electronic sensing method, the measured temperature thereof is more accurate than the temperature obtained through a light sensing element, such as an infrared ear thermometer.

Referring to FIG. 2C, FIG. 2C illustrates a top view of an ear tip in accordance with some embodiments of the present disclosure. The ear tip of FIG. 2C is similar to the ear tip 2 of FIG. 2A, and the differences therebetween are described below.

The ear tip of FIG. 2C further includes a capacitive sensor 22d disposed in the main body 21. In some embodiments, the capacitive sensor 22d includes a voltage and/or capacitance sensing area. In some embodiments, the capacitive sensor 22d includes a proximity sensor. In some embodiments, the capacitive sensor 22d may detect nearby objects by the electrical field created by the capacitive sensor 22d. In some embodiments, the electrical signals received via the capacitive sensor 22d may trigger the sensation of other biologically-relevant information. For example, the conductive element 22a and the conductive element 22b may use the electrical signals received via the capacitive sensor 22d as a trigger. Similarly, the thermistor 22c in FIG. 2B may use the electrical signals received via the capacitive sensor 22d as a trigger. For example, a controller associated with the capacitive sensor 22d may be configured to turn on or turn off the conductive elements depending on the electrical signals received via the capacitive sensor 22d. For example, a controller associated with the capacitive sensor 22d may be configured to turn on the conductive element, and the conductive element starts to collect information. By using the capacitive sensor 22d as a switch, the data-collecting function can be turned on only if the ear tip is worn, and energy can thus be conserved.

Referring to FIG. 2D, FIG. 2D illustrates a top view of an ear tip being used in accordance with some embodiments of the present disclosure. The ear tip of FIG. 2D is similar to the ear tip 2 of FIG. 2A, and the differences therebetween are described below.

The ear tip is in close proximity to a blood vessel 11 (such as the internal carotid artery or the internal jugular vein), the location of which provides an anatomical location having potential different from the potential of other areas of the human body. In addition, a wider potential difference can obtain a better signal to noise ratio. Some electrodes in the main body 21 are in close proximity to other electrodes, which helps establish a wider potential difference, thus enhancing the electrical signals and improving accuracy.

In some embodiments, the conductive elements 22a and 22b (or the electrodes), the thermistor 22c, and/or the capacitive sensor 22d can be embedded in the main body 21 as desired due to design requirements.

FIG. 3A, FIG. 3B, and FIG. 3C illustrate cross-sectional views of an ear tip in accordance with some embodiments of the present disclosure.

The ear tips of FIG. 3A, FIG. 3B, and FIG. 3C are similar to the ear tip 2 of FIG. 1, and the description of the similar or the same elements are omitted thereafter.

In FIG. 3A, the conductive element 22e is entirely embedded in the main body 21. The conductive pad 23 is partially exposed from the inner surface 21s3 of the central portion 21a. In FIG. 3B, the conductive element 22e is partially exposed from the outer surface 21s1 of the tail portion 21b. In FIG. 3C, the conductive element 22e is partially exposed from the inner surface 21s2 of the tail portion 21b.

In some embodiments, the conductive element 22e may be the conductive elements 22a and 22b (or the electrodes), the thermistor 22c, or the capacitive sensor 22d. In some embodiments, the arrangement, the relative wideness or thickness of the conductive elements may be designed according to design requirements.

Referring to FIG. 4A and FIG. 4B, FIG. 4A illustrates a cross-sectional view of a wearable device 4 in accordance with some embodiments of the present disclosure. FIG. 4B illustrates a top view of the wearable device 4. The wearable device 4 of FIG. 4 is similar to the wearable device 1 of FIG. 1, and the differences therebetween are described below.

The ear tip 2 of the wearable device 4 includes a protruding portion 41 shaped so as to correspond to a recessing portion defined in the housing 3. The protruding portion 41 may be used as a position confinement element when fitting the housing 3 in the ear tip 2. In some embodiments, the protruding portion 41 may help to quickly and precisely locate the conductive pad 23 to be contacted with the conductive pad 31. In some embodiments, the protruding portion 41 may prevent vertical displacement or shift, which may lead to wrong contacting between the conductive pad 23 and the conductive pad 31. In some embodiments, the protruding portion 41 may prevent horizontal displacement or shift (or circular rotation), which may lead to wrong contacting between the conductive pad 23 and the conductive pad 31. In some embodiments, the protruding portion 41 may engaged with the recessing portion defined in the housing 3. In some embodiments, the protruding portion 41 may non-rotatable in the recessing portion defined in the housing 3.

The positions and the numbers of the protruding portion 41 illustrated in FIG. 4A and FIG. 4B are for illustrative purpose only, and are not intended to limit the present disclosure. For example, there may be any number of protruding portion 41 due to design requirements. For example, the protruding portion 41 may be arranged in any position due to design requirements. For example, a central angle defined by two of the protruding portions may be less than 180 degrees, less than 120 degrees, less than 90 degrees, less than 60 degrees, less than 30 degrees, or less.

Similarly, positions and the numbers of the recessing portion defined in the housing 3 are for illustrative purpose only, and are not intended to limit the present disclosure. In some embodiments, the protruding portions 41 may have different shapes or sizes from each other for mistake proofing.

In some embodiments, a buckle portion 3t of the housing 3 and/or the bottom 21m may be used as a position confinement element (alone or in combination with the protruding portion 41) when fitting the housing 3 in the ear tip 2.

Figure 5A:
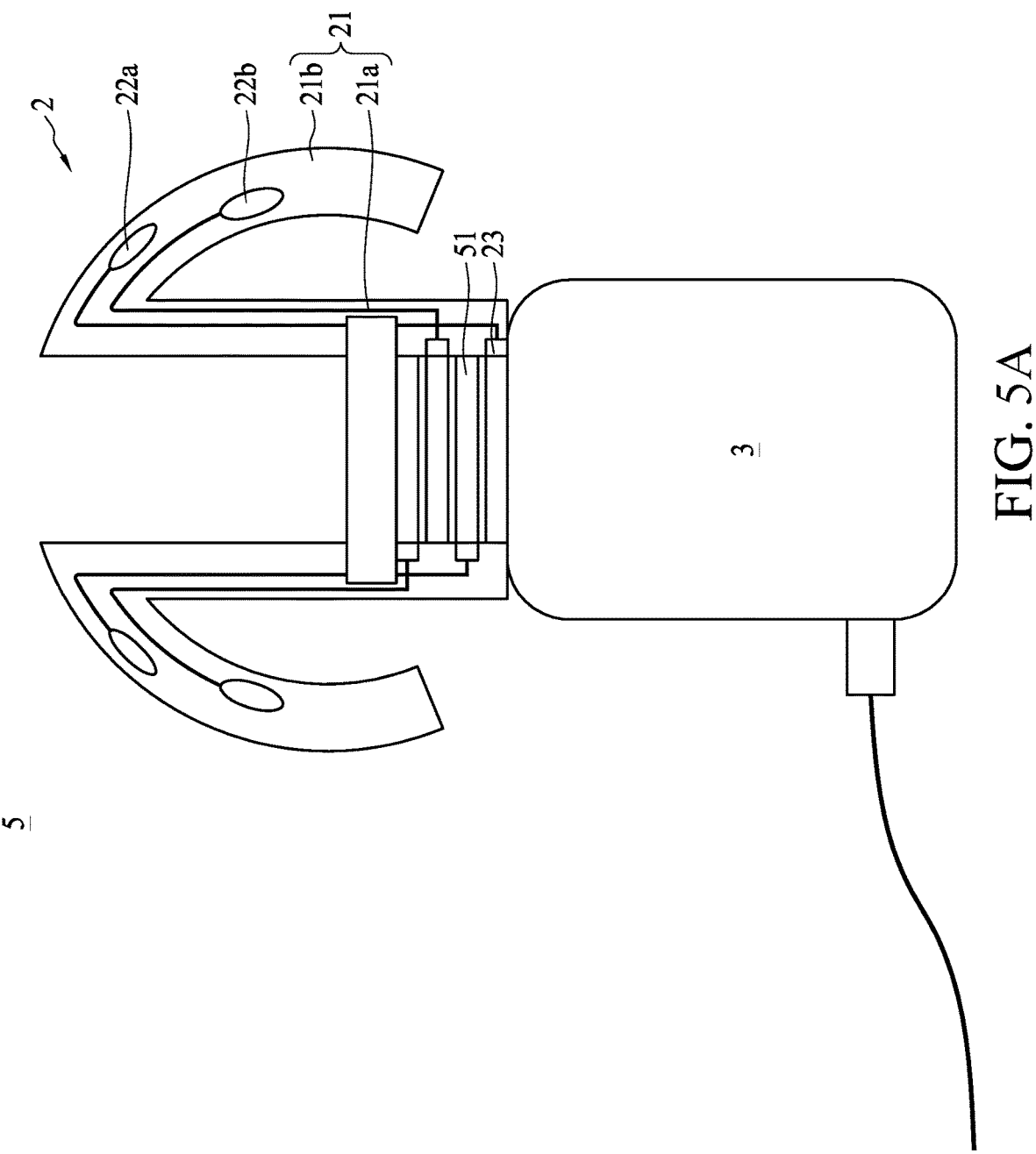
FIG. 5A illustrates a cross-sectional view of a wearable device in accordance with some embodiments of the present disclosure.

Referring to FIG. 5A, FIG. 5A illustrates a cross-sectional view of a wearable device 5 in accordance with some embodiments of the present disclosure. The wearable device 5 of FIG. 5A is similar to the wearable device 1 of FIG. 1, and the differences therebetween are described below.

The housing 3 of the wearable device 5 includes a conductive pad 51—circling or surrounding the portion of the housing 3—to be adapted to fit in the ear tip 2 of the wearable device 5. The ring shaped conductive pad 51 can be aligned with the conductive pad 23 of the ear tip 2 in one dimension (such as the height) without worrying about losing data if the ear tip 2 is rotated.

Figure 5B:
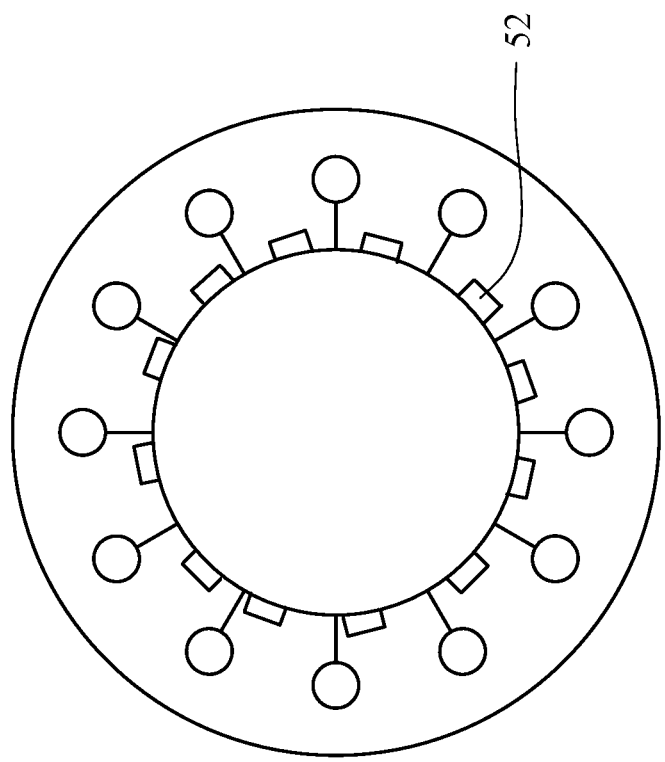
FIG. 5B illustrates a top view of an ear tip in accordance with some embodiments of the present disclosure.

Referring to FIG. 5B, FIG. 5B illustrates a top view of an ear tip 5' in accordance with some embodiments of the present disclosure. The ear tip 5' of FIG. 5B is similar to the ear tip 2 of FIG. 2A, and the differences therebetween are described below.

The ear tip 5' includes a plurality of conductive pads 52 separated from each other. The plurality of conductive pads 52 are arranged to circle or surround the portion of the housing 3 to be adapted to fit in the ear tip 5'. For example, two of the conductive pads 52 are at least partially overlapped in a direction surrounding the ear tip 5' (such as in a direction surrounding the central portion of the main body of the ear tip 5'.

Although the wearable device illustrated in FIG. 4, FIG. 5A and FIG. 5B has a specific corresponding configuration between the ear tip and the housing, the ear tip according to the present disclosure may be designed to be adapted to any other kind of housing, and is not limited to the structure disclosed therein.

Figure 6C:
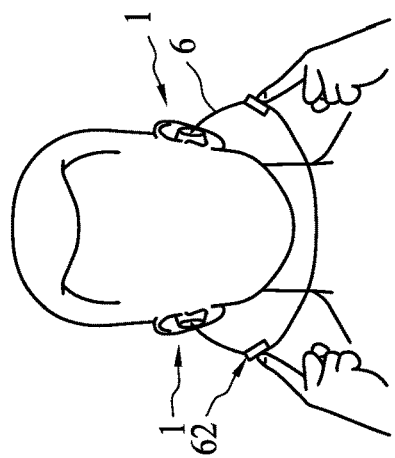
FIG. 6C illustrates a wearable device being used in accordance with some embodiments of the present disclosure.
Figure 6B:
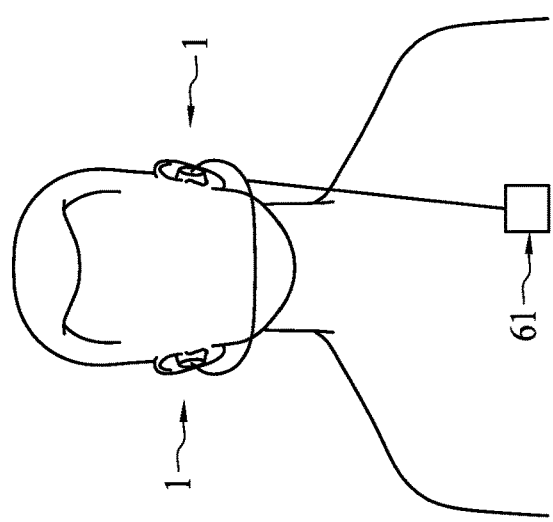
FIG. 6B illustrates a wearable device being used in accordance with some embodiments of the present disclosure.
Figure 6A:
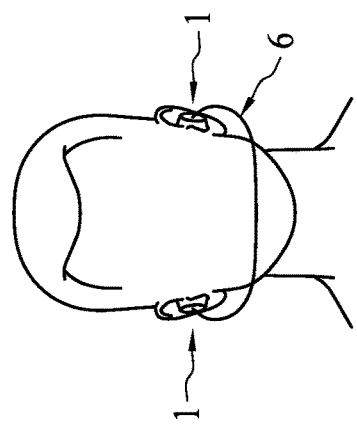
FIG. 6A illustrates a wearable device being used in accordance with some embodiments of the present disclosure.

FIG. 6A, FIG. 6B, and FIG. 6C illustrate a wearable device (such as the wearable device 1) under using circumstance in accordance with some embodiments of the present disclosure.

Referring to FIG. 6A, the left side and the right side of the wearable device 1 are connected through a wire or a cable 6. The electrical signals received from the left and right ear may be used to produce an ECG.

Referring to FIG. 6B, an ECG patch 61 may be used in combination with the wearable device 1. The ECG patch 61 may be attached to the chest of a user. The ECG patch 61 and the wearable device 1 may be anatomical locations having potentials different enough to allow obtaining a good signal to noise ratio.

Referring to FIG. 6C, an ECG patch 62 may be used in combination with the wearable device 1. For example, a left hand and/or a right hand of a user may be anatomical locations used in combination with the wearable device 1.

Figure 7:
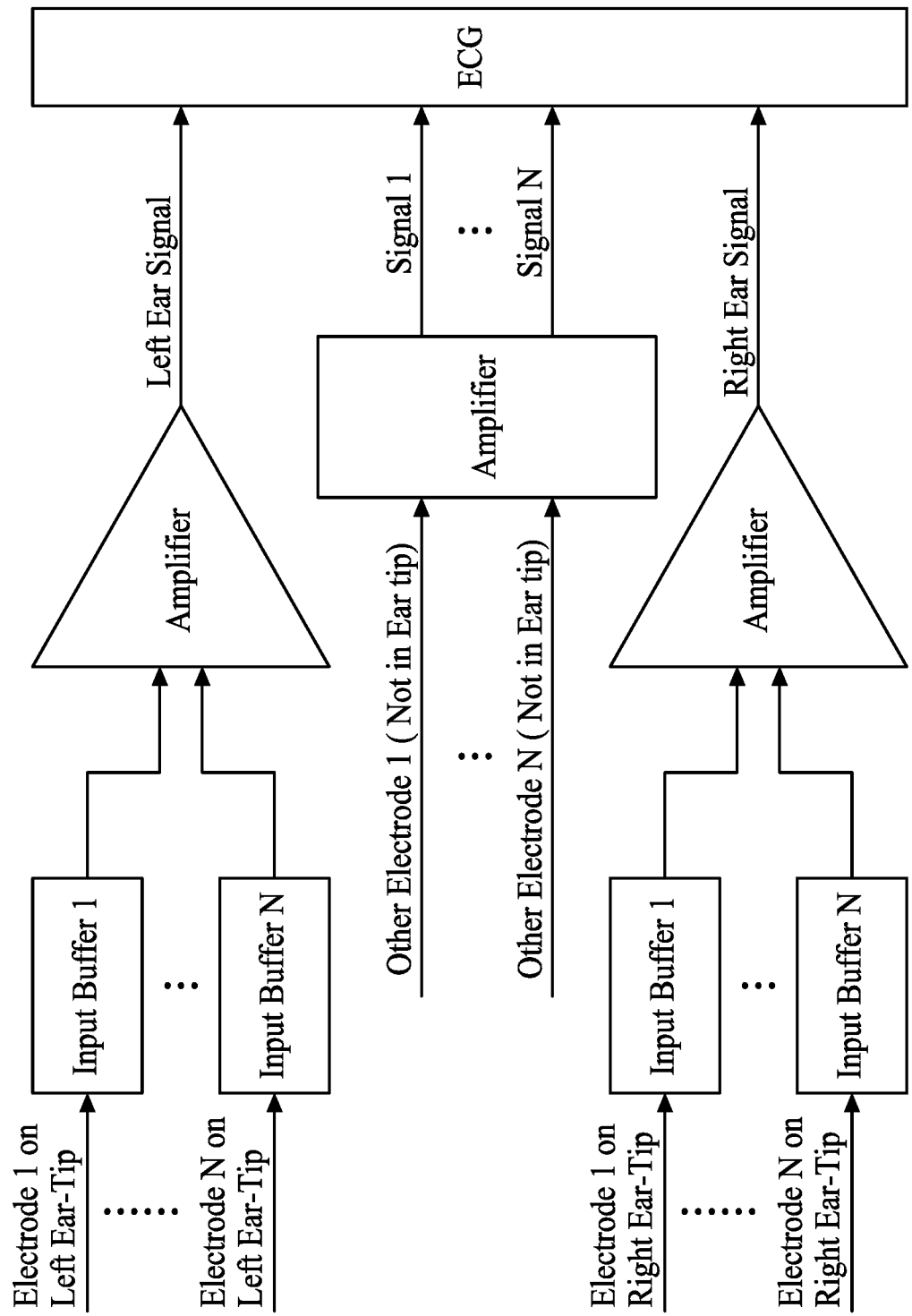
FIG. 7 illustrates a block diagram of an electronic apparatus or device coupled with a wearable device in accordance with some embodiments of the present disclosure.
Figure 8:
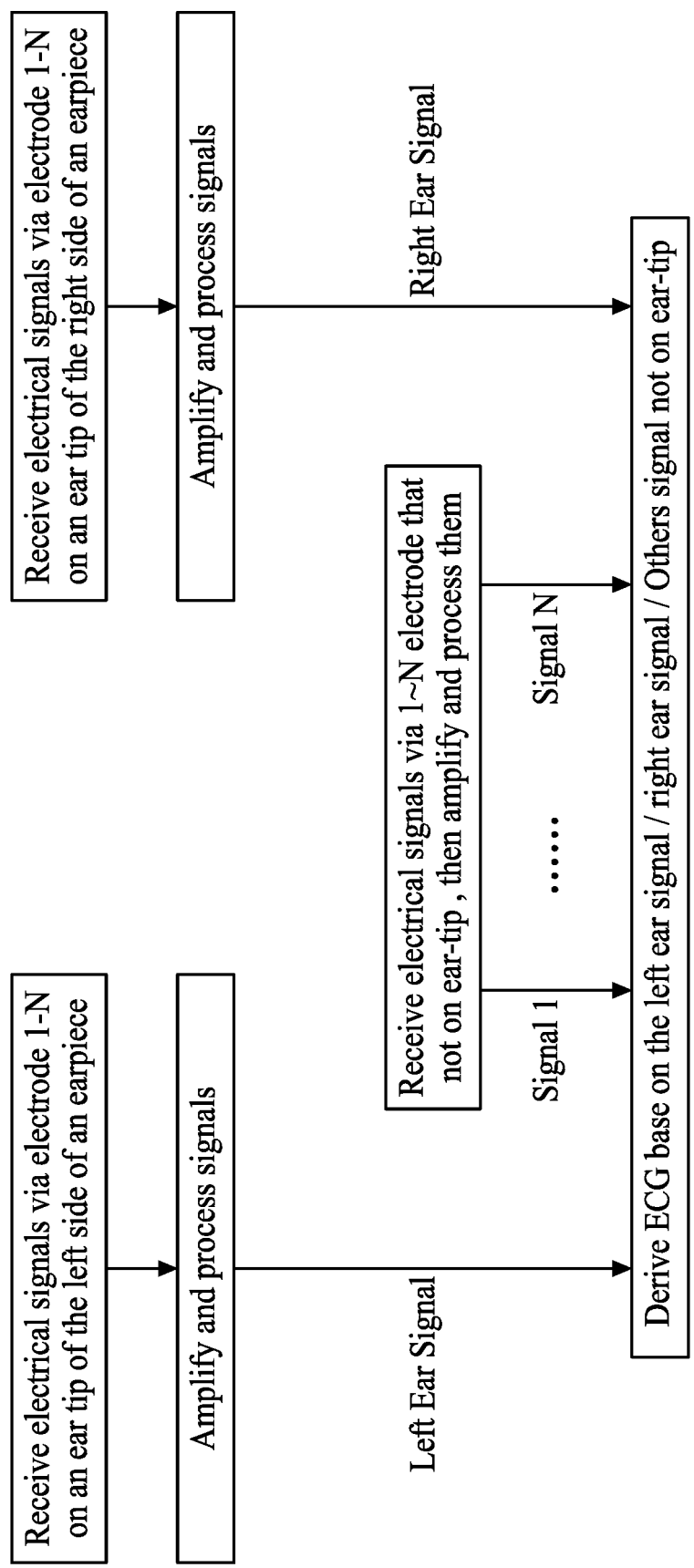
FIG. 8 illustrates one or more operations of a process flow for processing signals received from a wearable device in accordance with some embodiments of the present disclosure.

FIG. 7 illustrates a block diagram of an apparatus or device (such as an ECG machine) coupled with an earpiece (such as the wearable device 1) in accordance with some embodiments of the present disclosure. The one or more operations of a process flow of the system diagram illustrated in FIG. 7 are described below with reference to FIG. 8.

Electrical signals may be collected or received via the conductive element on the left-side and right-side ear tips (such as the conductive elements 22a and 22b (or the electrodes), the thermistor 22c, the capacitive sensor 22d) and the conductive element not on the ear tip (such as the ECG patch 61 and the ECG patch 62), or the combination thereof.

Each of the conductive elements is coupled to an input buffer, respectively. The input buffers may include high impedance amplifiers. The input buffers may be configured to match the high impedance of the conductive elements to the relatively low impedance of wires. In some embodiments, the input buffers are configured to perform noise cancellation for the signal received from the conductive elements 22a, 22b or other conductive elements.

Electrical signals outputted from the input buffers are transmitted to an amplifier. In some embodiments, the amplifier may be a single-ended amplifier or a differential amplifier. The amplifier may be configured to amplify the difference between the electrical signals (such as the potential different), and remove uncorrelated noise, and thus enhance signal-to-noise rate (SNR) of the electrical signals. Then the electrical signals may be coupled to an ECG machine to measure and derive an ECG information. In some embodiments, the number of the input buffers and the amplifiers are determined based on the number of the conductive elements (or electrodes) of the ear tips and the conductive element not on the ear tip (such as the ECG patch 61 and the ECG patch 62).

Spatially relative terms, such as "beneath," "below," "lower," "above," "upper," "left," "right" and the like, may be used herein for ease of description to describe one element or feature's relationship to another element(s) or feature(s) as illustrated in the figures. The spatially relative terms are intended to encompass different orientations of the device in use or operation, in addition to the orientation depicted in the figures. The apparatus may be otherwise oriented (rotated 90 degrees or at other orientations) and the spatially relative descriptors used herein may likewise be interpreted accordingly. It should be understood that when an element is referred to as being "connected to" or "coupled to" another element, it may be directly connected to or coupled to the other element, or intervening elements may be present.

As used herein, the terms "approximately", "substantially", "substantial" and "about" are used to describe and account for small variations. When used in conduction with an event or circumstance, the terms can refer to instances in which the event or circumstance occurs precisely as well as instances in which the event or circumstance occurs to a close approximation. As used herein with respect to a given value or range, the term "about" generally means within ±10%, ±5%, ±1%, or ±0.5% of the given value or range. Ranges can be expressed herein as from one endpoint to another endpoint or between two endpoints. All ranges disclosed herein are inclusive of the endpoints unless specified otherwise. The term "substantially coplanar" can refer to two surfaces within micrometers (μm) of lying along the same plane, such as within 10 μm, within 5 μm, within 1 μm, or within 0.5 μm of lying along the same plane. When referring to numerical values or characteristics as "substantially" the same, the term can refer to the values lying within ±10%, ±5%, ±1%, or ±0.5% of an average of the values.

The foregoing outlines features of several embodiments and detailed aspects of the present disclosure. The embodiments described in the present disclosure may be readily used as a basis for designing or modifying other processes and structures for carrying out the same or similar purposes and/or achieving the same or similar advantages of the embodiments introduced herein. Such equivalent constructions do not depart from the spirit and scope of the present disclosure, and various changes, substitutions, and alterations may be made without departing from the spirit and scope of the present disclosure.

What is claimed is:

1. An ear tip, comprising:
a main body, the main body including a central portion having a top and a tail portion extending from the top of the central portion, wherein the tail portion is around the central portion and configured to be in contact with an object to be detected;
a first conductive element at least partially embedded in the tail portion of the main body;
a second conductive element at least partially embedded in the tail portion of the main body and electrically spaced apart from the first conductive element; and
a conductive wire connecting with the first conductive element or the second conductive element, wherein the conductive wire is configured to transmit a signal from the first conductive element or the second conductive element to an internal surface of the central portion of the main body;
wherein the first conductive element is closer to the top of the central portion than the second conductive element is; and
wherein the first conductive element and the second conductive element are not entirely surrounding the central portion from a top view of the ear tip.

2. The ear tip of claim 1, wherein the conductive wire is embedded in the main body and sequentially extends along a bottom of the central portion, the top of the central portion, and then to the first conductive element or the second conductive element.

3. An ear tip, comprising:
a main body, the main body including a central portion having a top and a tail portion extending from the top of the central portion, wherein the tail portion is around the central portion and configured to be in contact with an object to be detected;
a first conductive element at least partially embedded in the tail portion of the main body;
a second conductive element at least partially embedded in the tail portion of the main body and electrically spaced apart from the first conductive element; and
a first conductive pad disposed on an internal surface of the central portion of the main body, wherein the first conductive pad is configured to transmit a signal from the first conductive element or the second conductive element to an external device;
wherein the first conductive element is closer to the top of the central portion than the second conductive element is; and
wherein the first conductive element and the second conductive element are not entirely surrounding the central portion from a top view of the ear tip.

4. The ear tip of claim 3, further comprising:
a second conductive pad disposed on the internal surface of the central portion of the main body and spaced apart from the first conductive pad;
wherein the first conductive pad is connected with the first conductive element, and the second conductive pad is connected with the second conductive element; and
wherein the first conductive pad and the second conductive pad are electrically separated from each other.

5. An ear tip, comprising:
a main body, the main body including a central portion having a top and a tail portion extending from the top of the central portion, wherein the tail portion is around the central portion and configured to be in contact with an object to be detected;
a first conductive element fully embedded within the tail portion of the main body;
a second conductive element fully embedded within the tail portion of the main body and electrically spaced apart from the first conductive element;

a conductive wire connecting with the first conductive element or the second conductive element, wherein the conductive wire is configured to transmit a signal from the first conductive element or the second conductive element to an internal surface of the central portion of the main body; and a first conductive pad disposed on the internal surface of the central portion of the main body, wherein the first conductive pad is configured to transmit the signal from the first conductive element or the second conductive element to an external device;

wherein the first conductive element is closer to the top of the central portion than the second conductive element is; and wherein the first conductive element and the second conductive element are not entirely surrounding the central portion from a top view of the ear tip.

6. The ear tip of claim 1, wherein the first conductive element and the second conductive element are not exposed from the tail portion of the main body.

7. The ear tip of claim 1, wherein the first conductive element and the second conductive element are entirely in contact with the tail portion of the main body.

8. The ear tip of claim 3, wherein the first conductive element and the second conductive element are fully embedded within the tail portion of the main body.

9. The ear tip of claim 8, wherein the first conductive element and the second conductive element are signally spaced apart from each other.

* * * * *